(12) United States Patent
Fink et al.

(10) Patent No.: US 7,747,030 B2
(45) Date of Patent: Jun. 29, 2010

(54) METHOD FOR IDENTIFYING A HEARING AID

(75) Inventors: Scott Raymond Fink, Apache Junction, AZ (US); Samuel L. Thomasson, Gilbert, AZ (US)

(73) Assignee: Zounds Hearing, Inc., Phoenix, AZ (US)

( * ) Notice: Subject to any disclaimer, the term of this patent is extended or adjusted under 35 U.S.C. 154(b) by 1169 days.

(21) Appl. No.: 11/357,362

(22) Filed: Feb. 17, 2006

(65) Prior Publication Data
US 2007/0195977 A1  Aug. 23, 2007

(51) Int. Cl.
*H04R 25/00* (2006.01)
(52) U.S. Cl. .................................. 381/315; 381/323
(58) Field of Classification Search ............ 381/314, 381/315, 60, 312
See application file for complete search history.

(56) References Cited

U.S. PATENT DOCUMENTS

| | | | | |
|---|---|---|---|---|
| 4,989,251 A | * | 1/1991 | Mangold | ............... 381/314 |
| 5,210,803 A | * | 5/1993 | Martin et al. | ............... 381/315 |
| 6,888,948 B2 | * | 5/2005 | Hagen et al. | ............... 381/314 |
| 2003/0100331 A1 | * | 5/2003 | Dress et al. | ............... 455/550 |
| 2009/0129619 A1 | * | 5/2009 | Nordahn | ............... 381/328 |

* cited by examiner

*Primary Examiner*—Fan Tsang
*Assistant Examiner*—Phylesha Dabney
(74) *Attorney, Agent, or Firm*—Paul F. Wille

(57) ABSTRACT

A hearing aid is identified by storing a first binary code in the hearing aid as a first identification code, storing a second binary code in the hearing aid as a default code, and replacing the default code with a second identification code if a second hearing aid is used by the person using the first hearing aid. The identification code includes a bit indicating for which ear the hearing aid is intended. If two hearing aids are used, the identification code of the first hearing aid is substituted for the default code in the second hearing aid and vice-versa, thereby pairing the first hearing aid with the second hearing aid and indicating that there are two hearing aids needed, even if one hearing aid should become lost or inoperative.

8 Claims, 2 Drawing Sheets

METHOD FOR IDENTIFYING A HEARING AID

FIELD OF THE INVENTION

This invention relates to apparatus and methods for communicating with at least one hearing aid and, in particular, to transferring data to and from a hearing aid using signals in the audible spectrum.

GLOSSARY

As used herein, the following words are intended to have the meanings given.

"Audible" is perceptible to one of ordinary, average, or normal hearing when the sound is not softer than or masked by other sounds or noise.

"Noise" is unwanted sound, whether periodic, random, or a mixture thereof.

"Hearing aid" is a device as presently defined by the U.S. Food and Drug Administration, 21 CFR 874.3300; viz. "a hearing aid is wearable sound amplifying device that is intended to compensate for impaired hearing. This generic type of device includes the air conduction hearing aid and the bone conduction hearing aid, but excludes the group hearing aid or group auditory trainer, master hearing aid, and tinnitus masker."

"Hearing aid calibrator and analysis system" is a device as presently defined by the U.S. Food and Drug Administration, 21 CFR 874.3310; viz. "a hearing aid calibrator and analysis system is an electronic reference device intended to calibrate and assess the electroacoustic frequency and sound intensity characteristics emanating from a hearing aid, master hearing aid, group hearing aid or group auditory trainer. The device consists of an acoustic complex of known cavity volume, a sound level meter, a microphone, oscillators, frequency counters, microphone amplifiers, a distortion analyzer, a chart recorder, and a hearing aid test box."

"Master hearing aid" is a device as presently defined by the U.S. Food and Drug Administration, 21 CFR 874.3330; viz. "a master hearing aid is an electronic device intended to simulate a hearing aid during audiometric testing. It has adjustable acoustic output levels, such as those for gain, output, and frequency response. The device is used to select and adjust a person's wearable hearing aid."

"Narrow band" is a concept related to the "Q" of a filter, both of which are somewhat soft concepts because neither says what the shape of the response curve looks like. For the sake of this disclosure, a narrow band filter has a bandwidth at −3 dB equal to approximately two percent of the center frequency. Thus, a 5 kHz filter is a narrow band filter if the bandwidth at −3 dB is 100 Hz. Narrower would be better, and preferred, but the tradeoff is cost.

Those of skill in the art recognize that, once an analog signal is converted to digital form, all subsequent operations can take place in one or more suitably programmed microprocessors. Reference to "signal," for example, does not necessarily mean a hardware implementation or an analog signal. Data in memory, even a single bit, can be a signal. In other words, a block diagram can be interpreted as hardware, software, e.g. a flow chart or an algorithm, or a mixture of hardware and software. Programming a microprocessor is well within the ability of those of ordinary skill in the art, either individually or in groups.

BACKGROUND

It has long been a goal in the art to communicate with a hearing aid for various purposes. Wired connections are known but undesirable because of the exposed connector in the hearing aid. It is known in the art to use a "wireless interconnection" to program hearing aids; see U.S. Pat. No. 6,888,948 (Hagen et al.). Transferring programming data to a hearing aid is disclosed. Transferring data from a hearing aid is not disclosed in the Hagen et al. patent.

U.S. Pat. No. 4,947,432 (Tøpholm) discloses programming a hearing aid using either RF or ultrasonic signals from a hand held controller and using identity codes to distinguish the hearing aids worn by a user from other hearing aids. U.S. Pat. No. 5,012,520 (Steeger) discloses not using "airborne sound transmission" and encoding and decoding the entire data stream to a hearing aid. U.S. Pat. No. 5,202,927 (Tøpholm) discloses programming the response of a hearing aid to suit ambient conditions. U.S. Pat. No. 5,909,497 (Alexandrescu) discloses acoustically coupling to a hearing aid, sending programming information with a leader to identify the data as program information, and detecting the leader to switch the hearing aid to a programming mode. The leader may include identification codes. U.S. Pat. No. 6,035,050 (Weinfurtner et al.) discloses a hand held control for programming and controlling a hearing aid. U.S. Pat. No. 6,115,478 (Schneider) discloses encoding a signal for a hearing aid by the presence and absence of signals in frequency sub-bands as generated by a sound card in a personal computer.

In general, the prior art describes systems for those familiar with, or at least comfortable with, sophisticated electronics. The fabled inability of people to program their video cassette recorders suggests that programmable hearing aids of the prior art may be more pleasing to the people who designed them than to the people who must use them. In short, there is a need for simplicity or, at least, the appearance of simplicity in programmable hearing aids.

Audiologists are presumably comfortable with sophisticated electronics but many situations arise when an audiologist is unavailable, either because of time or distance. Hearing aids can become lost or damaged for a variety of reasons, particularly for users at each end of the age spectrum. It would be a great convenience to be able to program a hearing aid at home or wherever a user happened to be and not require a trained technician for programming or adjustment.

Hearing aids are frequently provided for both ears. Although it is known in the art to provide some sort of identity signal, there is a need for a system that provides a unique identity for each hearing aid, yet the identification process is invisible to the user.

As defined in the art, "hearing aid" and "master hearing aid" are separate elements. It is desired to provide a single device that performs both functions. By having a hearing aid perform a hearing test, one has a test device that exactly matches the hearing aid because they are one and the same. The location in the ear is the same for test and use, and the chamber in the ear canal is the same for test and use. The results are inherently more accurate than with separate audiometers and hearing aids.

Although many "multiband" digital hearing aids are on the market, many with sixteen or more frequency bands, a hearing test typically uses only five or six different frequencies and the results are extrapolated for the sixteen frequency bands. Accuracy of a hearing test can be further improved by testing within each band available in a hearing aid.

Hearing tests often take place in an individual having one ear with distinctly better hearing than the other ear. It is desired to provide a test that accommodates such situations and reliably and accurately tests each ear independently.

A hearing aid that provides noise cancellation in the ear canal is known in the art. The sounds in the ear canal are detected by a microphone in a hearing aid and are used to program a filter coupled to an external microphone in the hearing aid for reducing the sounds to a minimum. It is desired to combine noise cancellation with a hearing test that does not need a special chamber or special test apparatus. By using noise cancellation, a hearing test is made more accurate because the threshold of hearing is lowered (less noise obscuring a test signal).

Although hand held controls for hearing aids are known, such controls tend to be relatively large complicated devices with many buttons or switches. Of the patents named above, the Weinfurtner et al. patent describes the simplest, with ten buttons and a display. A corresponding product does not appear to be on the market from the patent owner. The patent owner does sell a controller with a display and a few buttons for adjusting amplitude and "program" (frequency response). The controller does not program a hearing aid, it merely selects one previously stored in the hearing aid by other means.

In view of the foregoing, it is therefore an object of the invention to provide method for identifying hearing aids that indicates for which ear the hearing aid is intended.

A further object of the invention is to provide a system for identifying a replacement hearing aid.

Another object of the invention is to provide a method for pairing hearing aids to indicate indicating that there are two hearing aids needed, even if one hearing aid should become lost or inoperative.

SUMMARY OF THE INVENTION

The foregoing objects are achieved by this invention in which a hearing aid is identified by storing a first binary code in the hearing aid as a first identification code, storing a second binary code in the hearing aid as a default code, and replacing the default code with a second identification code if a second hearing aid is used by the person using the first hearing aid. The identification code includes a bit indicating for which ear the hearing aid is intended. If two hearing aids are used, the identification code of the first hearing aid is substituted for the default code in the second hearing aid and vice-versa, thereby pairing the first hearing aid with the second hearing aid and indicating that there are two hearing aids needed, even if one hearing aid should become lost or inoperative.

BRIEF DESCRIPTION OF THE DRAWINGS

A more complete understanding of the invention can be obtained by considering the following detailed description in conjunction with the accompanying drawings, in which.

DETAILED DESCRIPTION OF THE INVENTION

Figure 1:
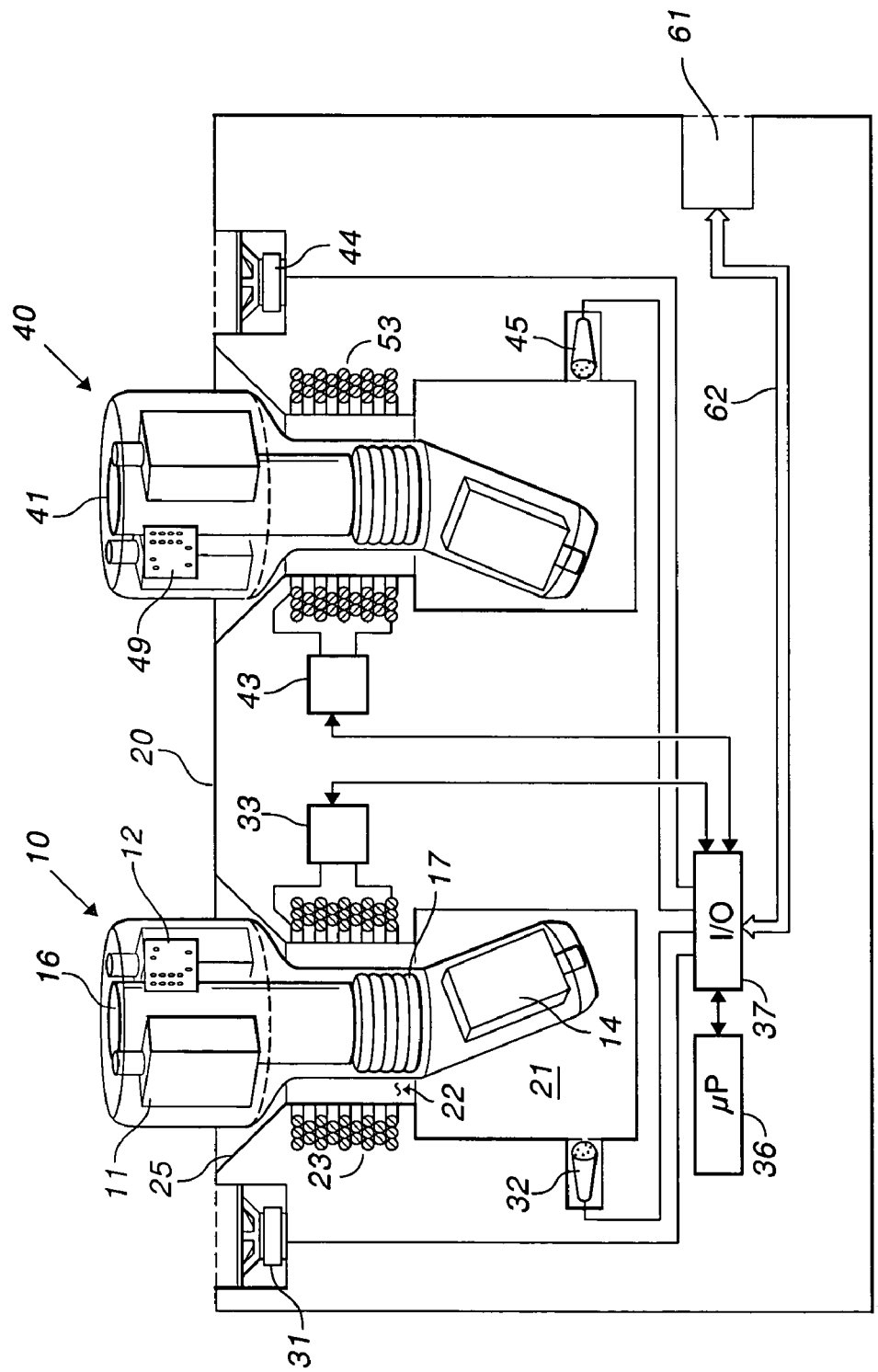
FIG. 1 is a partial block, partial phantom drawing illustrating a pair of hearing aids in a charger constructed in accordance with the invention.

In FIG. 1, a pair of hearing aids are inserted into charger 20 for charging and conveying information among the hearing aids and a hand held control (not shown in FIG. 1. Hearing aid 10 includes at least one microphone, such as microphone 11, a flex circuit or integrated circuit 12 containing a microprocessor for signal processing and other tasks, speaker 14, and rechargeable battery 16 for power. Beneath battery 16 is inductor 17, which is electrically coupled to circuit 12, as are the other electrical components. Dedicated electronics can be used instead of programmable electronics but programmable electronics are preferred.

The lower portion of hearing aid 10, containing speaker 14, fits easily within chamber 21. The middle portion of hearing aid 10 is located in chamber 22 within inductor 23. Inductor 17 and inductor 23 are approximately concentric but, as one of the advantages of the invention, alignment and position are not critical. The outer or upper portion of hearing aid 10 fits within conical depression 25, which provides a self-centering action for the type of hearing aid illustrated. Conical depression 25 terminates in chamber 22.

The preferred medium for communication with the hearing aids is sound, using the microphone and speaker already in the hearing aid. In accordance with a preferred embodiment of the invention, charger 20 includes speaker 31 and microphone 32 for this purpose. Given the two-way communication between the charger and the hearing aid, there is no limit on the content of the communication. For example, the charger could also serve as an interface for programming a microprocessor in the hearing aid. Using suitable tones, or sets of tones, to represent logic ones and zeros, the hearing aid can transmit a first code indicating the level of charge and a second code indicating the rate of charge. If, for example, the coupling between inductors 17 and 23 happened to be particularly good, the hearing aid could "ask" the charger to reduce the current through inductor 23 to reduce the rate of charge, thereby preventing overheating.

As illustrated in FIG. 1, speaker 31 and microphone 32 are located adjacent chamber 21. Hearing aid 10 does not form a seal with charger 20 and there is sufficient coupling between speaker 31 and microphone 11. Speaker 31 can be located closer to microphone 11, if desired. If one wanted the charging to be inaudible, one could position speaker 31 closer to microphone 11 and put the speaker and the hearing aid in an enclosed space.

Power supply 33 provides charging power to hearing aid 10 by way of inductor 23. A signal at a current of a few tens of milliamperes and a frequency of 100 kHz-500 kHz is effective. Power supply 33 is controlled by and communicates with microprocessor 36 by way of input-output (I/O) interface 37. Interface 37 also drives speaker 31 and receives signals from microphone 32. While shown as separate elements, it is known in the art that many commercially available microprocessors have analog inputs and include analog to digital (A/D) converters on the same semiconductor chip as the computer portion of the microprocessor. Thus, "microprocessor" is intended to include computing and logic capability and suitable I/O, whether on a single semiconductor chip or on plural chips.

As illustrated in FIG. 1, charger 20 includes receptacles for two hearing aids. Hearing aid 40 includes battery 41, which is charged by power supply 43 under the control of microprocessor 36. Although the operation is the same, the charging of battery 41 is completely independent of the charging of battery 16.

The presence of a hearing aid can be detected by power supply 33 or power supply 43, for example, by sensing a change in inductance in inductor 23 or inductor 53. Alternatively, presence can be sensed acoustically by recognizing the sound of a hearing aid being inserted into charger 20 or by a sound in microphone 32 or 45. Other acoustic or magnetic presence detectors can be used instead. More simply, one can simply use a switch (not shown) for each receptacle to alert microprocessor 36 that a hearing aid has been inserted and to begin a charging cycle for that receptacle.

Charger 20 further includes receptacle 61 for receiving a hand held controller (not shown in FIG. 1). I/O circuit 37 provides two way communication over bus 62 with the controller. An acoustic coupling, as used for the hearing aids, can be used instead and is preferred. In accordance with one aspect of the invention, the charger, the controller, and the programmer (FIG. 3) all have microphones and speakers for two way communication among the devices.

Figure 2:
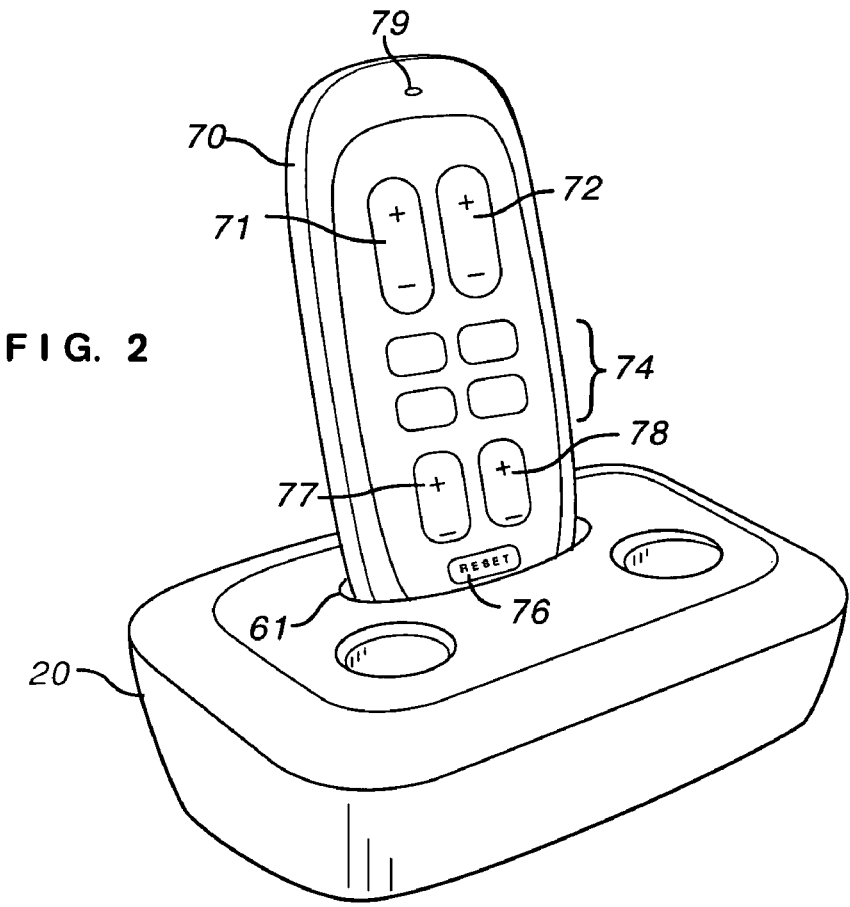
FIG. 2 is a perspective view of a controller and charger constructed in accordance with a preferred embodiment of the invention.

FIG. 2 is a perspective view of controller 70 resting in receptacle 61 in charger 20. Controller 70 provides day to day operation of one or more hearing aids and includes at least left volume control 71, right volume control 72, and keypad 74 for selecting a frequency response suited to the named environments. In one embodiment of the invention, keypad 74 includes four keys labeled "QUIET," "DINNER," "PARTY," and "MUSIC." These frequency responses are derived from the test results when the hearing aid is calibrated. Controller 70 preferably also includes "RESET" switch 76, for returning a hearing aid to its calibrated setting after testing, "BASS" control 77, and "TREBLE" control 78. The latter controls affect frequency response as the names indicate. Controller 70 also includes speaker 79 for communicating with the hearing aids. A microphone (not shown in FIG. 2) is located in receptacle 61 for receiving signals from charger 20 or from the hearing aids.

When the hearing aids are worn by the user, controller 70 communicates with the hearing aids by way of speaker 79. In a preferred embodiment of the invention, integrated circuits 12 and 49 (FIG. 1) each include a narrow band pass filter having a center frequency at some audible frequency, e.g. 7 kHz. Communication is preferably asynchronous. Controller 70 transmits a sonic signal at this frequency and the presence or absence of a signal at a particular time indicates a one or a zero. Thus, for example, increasing volume in the left ear is achieved by pressing the upper portion of button 71. An address prefix is included for selecting the appropriate hearing aid, followed by the command for increasing volume. If only a single hearing aid is used, the prefix is omitted and either button 71 or 72 increases volume. Because of the data shared among the units, controller 70 "knows" whether there is one hearing aid in use or two hearing aids.

Other modulation techniques can be used but asynchronous amplitude modulation is preferred for simplicity. Check sums and other error detecting techniques known per se in the art can also used. If a user, for example, pushes a button for increasing volume in a hearing aid, and there is an error, the hearing aid is preferably programmed to indicate an error for the user by an alarm such as a beep or a blinking light and sending a message to the controller or programmer, or both, that there was an error. Simple messages take less than one second to transmit and feedback is therefore relatively immediate.

Figure 3:
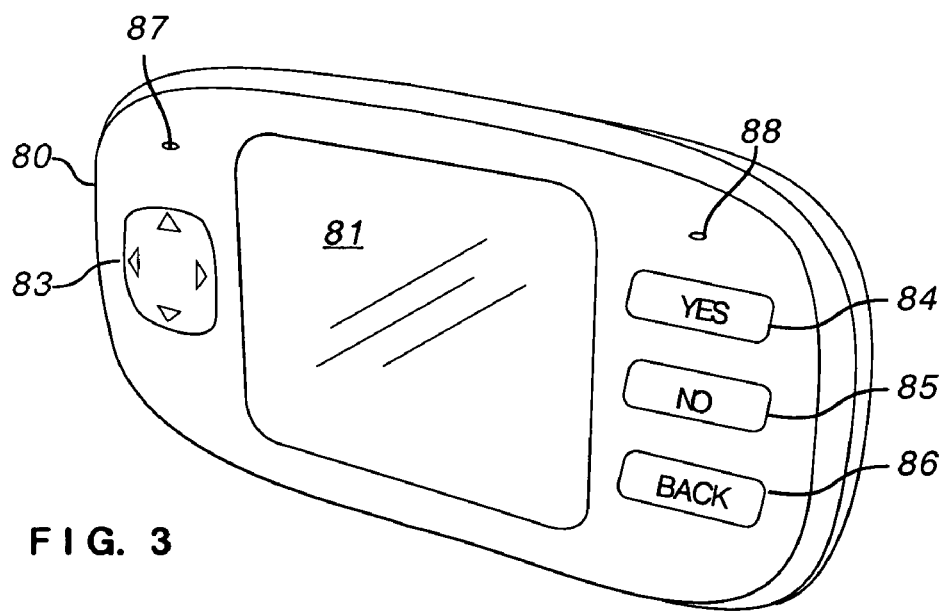
FIG. 3 is perspective view of a programmer constructed in accordance with a preferred embodiment of the invention.

A programmer constructed in accordance with a preferred embodiment of the invention is illustrated in perspective view in FIG. 3. Programmer 80 includes a display panel 81, preferably a backlit, liquid crystal display that can provide both text and images, such as graphs, and keypad 83, including arrows arranged as shown. The keypad and display 81 are programmable, that is, the function assigned to a given key can change depending upon the operation taking place and the display can contain text and graphics in any arrangement. Programmer 80 also includes selection keys 84, 85, and 86 that, when actuated, provide the response indicated; viz. "YES," "NO," or "BACK." Programmer 80 also includes speaker 87 and microphone 88 for two way communication with the other devices. The microphone and speaker are illustrated on the front of programmer 80 but are preferable on opposite sides for greater acoustic isolation.

In FIG. 1, hearing aid 10 and hearing aid 40 are programmed with a unique serial number stored in memory in each hearing aid. When microprocessor 36 detects the presence of two hearing aids, the hearing aids are requested to transmit at least the lower order bits of their serial numbers, i.e. a portion of the serial number. The number of bits actually transmitted is a trade-off between the probably of accidental duplication and transmit time. For example, eight bits can uniquely identify two hundred and fifty-six hearing aids. The probability of two hearing aids having the same last eight bits is thus one in two hundred and fifty-six—a reasonably low probability.

In accordance with one aspect of the invention, microprocessor 36 then sends the eight bits from one hearing aid to the other hearing aid, and vice-versa. Now the hearing aids are paired and the microprocessor can detect a new hearing aid if a hearing aid is lost or destroyed. If a hearing aid does not transmit a second serial number, or transmits numbers not recognized by the programmer, then a new hearing aid must be present. If the programmer 80 is turned on, then the user is told a new hearing aid was detected and is asked if the new hearing aid should be programmed. If the answer is yes, then the programmer sends data to the appropriate hearing aid, reproducing the missing hearing aid.

In accordance with another aspect of the invention, a left and right convention is also used. In a preferred embodiment of the invention, the lowest order bit indicates hand, left or right. This enables the controller to provide a further check on the hearing aids before programming. It also simplifies and provides much more rapid control of the hearing aids in use because only a single bit distinguishes the two. Thus, the address of a hearing aid in use is either an odd number or an even number. In a preferred embodiment of the invention, serial numbers are not programmable by a user but are stored in read only memory. Programming is transparent to the user, who merely says "yes" or "no" to the prompts on display 81.

In accordance with another aspect of the invention, each hearing aid is calibrated during manufacture to a specific SPL (sound pressure level) in each band. This provides a user with a calibrated instrument for noise cancellation and hearing test. The initial, default, or "unprogrammed" state of a new hearing aid is a uniform amplitude response across the available spectrum. The calibration can take place in apparatus substantially like that shown in FIG. 1, except that a cover is added to create a chamber for the hearing aids and exclude noise.

A hearing test is initiated by selection from a menu. The display then asks "which ear" and the user presses, for example, the left arrow on button 83 to select the left ear. The display asks if hearing aids are inserted in each ear and turned on. If the answer is "yes," programmer 80 issues a noise cancellation command for the left ear. Optionally, programmer 80 issues a command for background noise in the right hearing aid to reduce the chance of cross-coupling during the test. The user is then told to press selection button 84 when a tone is heard in the left ear. Programmer 80 issues a command to produce a tone at a particular frequency and progressively increases the amplitude until button 84 is pressed or until an internal safety limit is reached. A sequence of tones is produced, preferably in random order.

In accordance with another aspect of the invention, the tones produced match the center frequencies of the band pass filters in the hearing aid. In this way, there is no interpolation of five or six data points to sixteen or more bands. The data matches the hearing aid as closely as possible and provides a better fit for the user. After the last tone, the hearing aid is programmed in accordance with the results of the test. Throughout the test, the user is given an opportunity to start over on a given tone or to start over from the beginning. After the first hearing aid is programmed, the process is repeated for the other hearing aid, if any.

The invention thus provides a device that is both hearing aid and master hearing aid. A more accurate test and more accurate compensation for hearing impairment is provided than obtainable in the prior art. The hearing test accurately tests each ear independently and minimizes the effect of cross-talk. Thus, the invention provides a user controlled hearing test that is accurate even when the user has one ear with distinctly better hearing than the other ear. The invention also provides a hand held controller for hearing aids that is easy to use and a system that identifies hearings aids and is easy for the user to operate. The system recognizes when a new hearing aid is added and can program a replacement hearing aid according the same parameters as the hearing aid being replaced. The test and corrective device are one and the same, thereby enabling greater accuracy than available in the prior art. Most importantly, a haring aid can be programmed wherever the user is, within reason. Obviously, a relatively quiet room is needed for best results.

Having thus described the invention, it will be apparent to those of skill in the art that various modifications can be made within the scope of the invention. For example, even though the controller performs a hearing test, this feature or other features can be locked out to prevent accidental or inappropriate use. The invention is particularly useful for hearing aids, wherein space is at a premium, but the invention can be used for other devices for assisting hearing. Any bit in the identification code could be used for indicating handedness. For example, instead of using the least significant bit (odd/even), one could use the most significant bit (positive/negative) of a signed number. Using the least significant bit is preferred.

What is claimed as the invention is:

1. A method for identifying a hearing aid, said method comprising the steps of:
   storing a first binary code in a first hearing aid as a first portion of an identification code;
   storing a default code in the first hearing aid as a second portion of the identification code; and
   replacing the default code with at least a portion of the identification code of a second hearing aid if the second hearing aid is used by the person using the first hearing aid; thereby linking the two identification codes.

2. The method as set forth in claim 1 wherein the identification code of the first hearing aid includes a bit indicating for which ear the hearing aid is intended.

3. The method as set forth in claim 1 wherein the identification code of the first hearing aid is odd or even depending upon for which ear a hearing aid is intended.

4. A method for identifying a pair of hearing aids, said method comprising the steps of:
   storing a first binary code in a first hearing aid as a first portion of a first identification code;
   storing a second binary code in the first hearing aid as a second portion of the first identification code;
   storing a third binary code in a second hearing aid as a first portion of a second identification code;
   storing a fourth binary code in the second hearing aid as a second portion of the second identification code;
   replacing the second binary code with the first portion of the second identification code;
   replacing the fourth binary code with the first portion of the first identification code;
   thereby pairing the first hearing aid with the second hearing aid and indicating that there are two hearing aids needed, even if one hearing aid should become lost or inoperative.

5. The method as set forth in claim 4 wherein each identification code includes a bit indicating for which ear the hearing aid is intended.

6. The method as set forth in claim 4 wherein each identification code is odd or even depending upon for which ear a hearing aid is intended.

7. The method as set forth in claim 4 wherein each identification code is positive or negative depending upon for which ear a hearing aid is intended.

8. The method as set forth in claim 4 wherein the second binary code and the fourth binary code are the same.

* * * * *